United States Patent
Richmond

(10) Patent No.: US 6,945,779 B2
(45) Date of Patent: Sep. 20, 2005

(54) TOOTH INCLINATION ASSESSMENT

(75) Inventor: Stephen Richmond, Vale of Glamorgan (GB)

(73) Assignee: University of Wales College of Medicine, Cardiff (GB)

( * ) Notice: Subject to any disclaimer, the term of this patent is extended or adjusted under 35 U.S.C. 154(b) by 221 days.

(21) Appl. No.: 10/220,492
(22) PCT Filed: Mar. 5, 2001
(86) PCT No.: PCT/GB01/00948
§ 371 (c)(1), (2), (4) Date: Nov. 29, 2002
(87) PCT Pub. No.: WO01/64130
PCT Pub. Date: Sep. 7, 2001

(65) Prior Publication Data
US 2003/0203335 A1 Oct. 30, 2003

(30) Foreign Application Priority Data
Mar. 3, 2000 (GB) .............................. 0005053

(51) Int. Cl.⁷ ............................................. A61C 19/04
(52) U.S. Cl. ......................................... 433/72; 433/44
(58) Field of Search .............................. 433/72, 44, 55, 433/56

(56) References Cited

U.S. PATENT DOCUMENTS
4,762,491 A 8/1988 Bolton

FOREIGN PATENT DOCUMENTS
DE 17 66 099 7/1971

Primary Examiner—Cary E. O'Connor
Assistant Examiner—Candice C. Stokes
(74) Attorney, Agent, or Firm—Young & Thompson

(57) ABSTRACT

A tooth inclination apparatus for allowing assessment of the angle of inclination of an incisor tooth or cast thereof includes a plane element providing a flat datum surface for resting against e.g. the upper molars in the maxillary plane. From the underside of the plane element projects a protractor portion with a graduated angular scale which measures the angular deviation of an indicator pin pivoted to the plane member and moved to contact the tooth whose inclination is being measured. Other mechanical or electro-optic devices may be used to determine the inclination of the incisor relative to the datum surface.

11 Claims, 2 Drawing Sheets

TOOTH INCLINATION ASSESSMENT

BACKGROUND OF THE INVENTION

This invention relates to the assessment of the inclination of the left, right, upper or lower incisors relative to a reference such as the maxillary plane or the mandibular plane respectively, or the occlusal plane.

The evaluation of maxillary and mandibular incisor inclinations is an important aspect of orthodontic treatment planning, assessing treatment progress, as well as determining treatment outcome. Incisor inclination has traditionally been assessed by lateral cephalometric radiographic analysis. However, lateral cephalometric radiograph derived axial inclinations of incisors are prone to large digitised errors. In addition, radiographs may cause a small but significant mitotic risk.

SUMMARY OF THE INVENTION

It is an aim of this invention to provide a valid, reliable, simple, inexpensive and non-invasive method and apparatus for recording incisor inclination.

According to one aspect, this invention provides a tooth inclination assessment apparatus for allowing assessment of the angle of inclination of an incisor tooth or cast thereof in or from the human or animal body, which apparatus comprises:

a datum element defining a generally flat datum surface for being placed in use against two or more upper or lower molars or pre-molars thereby to become generally aligned with the respective mandibular or maxillary plane, and an angular detector associated with said datum element for detecting the angular disposition relative to said datum surface of at least one of the upper or lower incisors respectively.

Preferably said angular detector comprises an indicator member movably mounted with respect to said datum element and arranged in use to be moved into contact with the tooth whose angle of inclination is to be measured, and an angle measurer for determining the angular orientation of said indicator member relative to said datum element.

Preferably said indicator member is pivotally mounted with respect to said datum element.

In one embodiment said measurer comprises a graduated angular scale whereby the angle of deflection of the indicator member relative to said datum member may be read off visually. Alternatively, said angular detector and/or said measurer could comprise a solid state sensor which detects the angle of inclination of the respective incisor either by detecting the angle of the indicator member if used, or by direct detection of the angle of the incisor. The nature, construction and operation of such electronic or electro-optic devices will be well known to those skilled in the art.

Preferably said indicator member extends to opposite sides of said datum surface, to define a tooth contact portion to one side, and a measuring portion to the other, to cooperate with said angle measurer.

Preferably said datum element and said angle measurer are made up from a folded sheet element blank e.g. of paper or card plain or laminated, or of plastics material, suitably shaped.

Preferably said sheet element blank comprises two generally symmetric portions which fold together to define said first element, together with a bridging tab portion which is connected to an angular scale portion.

Preferably, said indicator member includes a shaft which is rotatably located in the fold region between said two symmetric portions.

The invention also extends to a kit comprising said sheet element blank in generally flat form together with an indicator element.

According to another aspect, this invention provides a method of assessing the angle of inclination of an incisor tooth or a cast thereof in or from the human or animal body, which comprises applying to two or more of the upper molar or lower molars or pre molars a flat datum surface thereby to be generally aligned with the maxillary or mandibular plane respectively, said datum surface having associated therewith an angular detector for detecting the angular disposition of at least one of the incisors, and thereby determining the angular orientation of said incisor relative to said datum surface.

Preferably said angular detector comprises an indicator member rotatable mounted with respect to said datum surface.

Whilst the invention has been described above, it extends to any inventive combination of the features set out above or in the following description.

The invention will now be described in detail by way of example only, reference being made to the accompanying drawings in which.

DESCRIPTION OF THE PREFERRED EMBODIMENT

Figure 1:
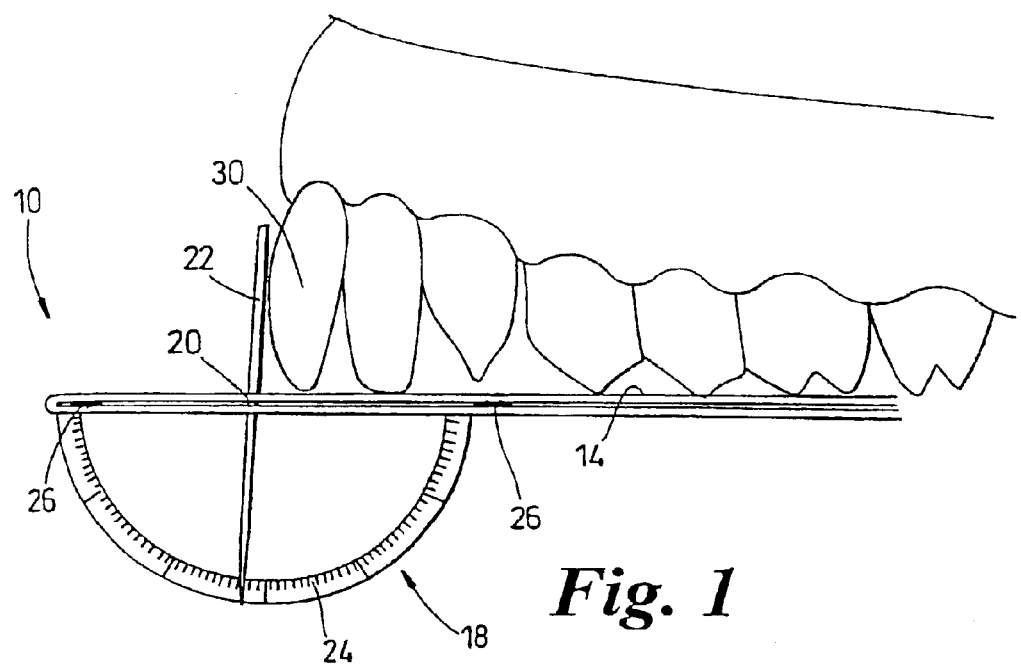
FIG. 1 is a side view of an embodiment of the tooth inclination protractor of this invention in use on a dental cast measuring the inclination of an upper incisor to the maxillary plane.

Referring to the Figures, the tooth inclination protractor 10 comprises a blank 12 of suitable card or plastic sheet folded double about fold line I to provide a flat datum surface 14. From one side of the blank 12 projects a tab 16 which terminates in a graduated semicircular protractor portion 18. Rotatably secured at the origin of the protractor portion 18 is the shaft 20 of an indicator pin 22. One half of the pin projects below the datum surface as viewed in FIG. 1 to terminate at the scale 24 of the protractor portion 18, whilst the other half of the pin projects upwardly to be pivoted into contact with the labial surface of the incisor tooth whose surface of inclination is to be measured.

The blank 12 may be provided with adhesive regions 26 on the meeting surfaces which define the datum surface 14, with an interruption to receive the shaft 20 of the indicator pin. Likewise the meeting surfaces of the datum surface and the tab 16 may carry adhesive regions.

For flat pack, the blank may be stored in a flat form with suitable release sheets (not shown) on the adhesive regions, and instructions on how to make up the tooth inclinator protractor by positioning the indicator pin 22 at the correct location at the fold line I, removing the release sheets and then folding the blank about fold line I. Thereafter the blank is folded by 180° about fold line II to fold the tab 16 against the blank, and then by 90° about fold line III to place the protractor portion 18 projecting normally from the datum surface, and adjacent the indicator pin 22, to produce the tooth inclination protractor as shown in FIG. 1.

Figure 2:
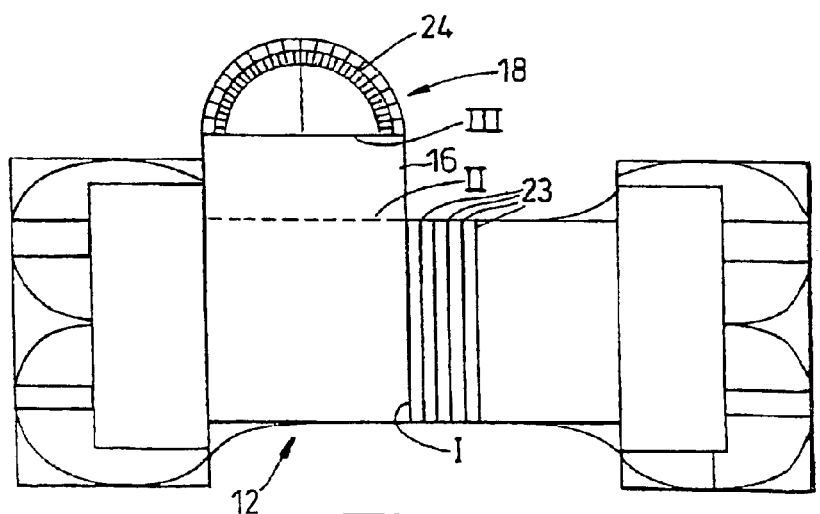
FIG. 2 is a plan view of a blank for forming the major part of a tooth inclination protractor of an embodiment of this invention.
Figure 3:
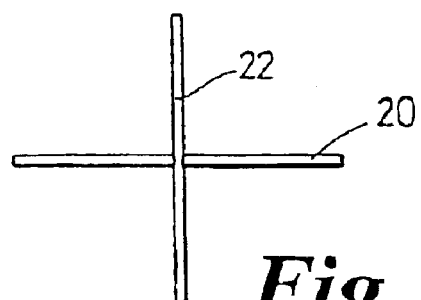
FIG. 3 is a view of a rotatable indicator pin for use with the blank of FIG. 2.

The blank is preferably printed on one side only with the alignment markings as shown in FIG. 2. The protractor may carry lines 23 on the middle of the protractor to allow overjet to be measured.

To measure the tooth inclination in say the upper (maxillary) set of teeth, the protractor is placed in the mouth so that the datum surface 14 rests against the upper molars to define a reference surface, with the incisor whose angle is to be measured disposed adjacent the indicator pin, and the protractor portion 18 projecting downwardly. The pin 22 is then rotated against the lateral surface of the incisor 30 at its maximum bulbosity so that the area above and below the contact is equal so that the pin 22 is then tangential to the point of contact. The angle of inclination is then read off the protractor scale.

Figure 4:
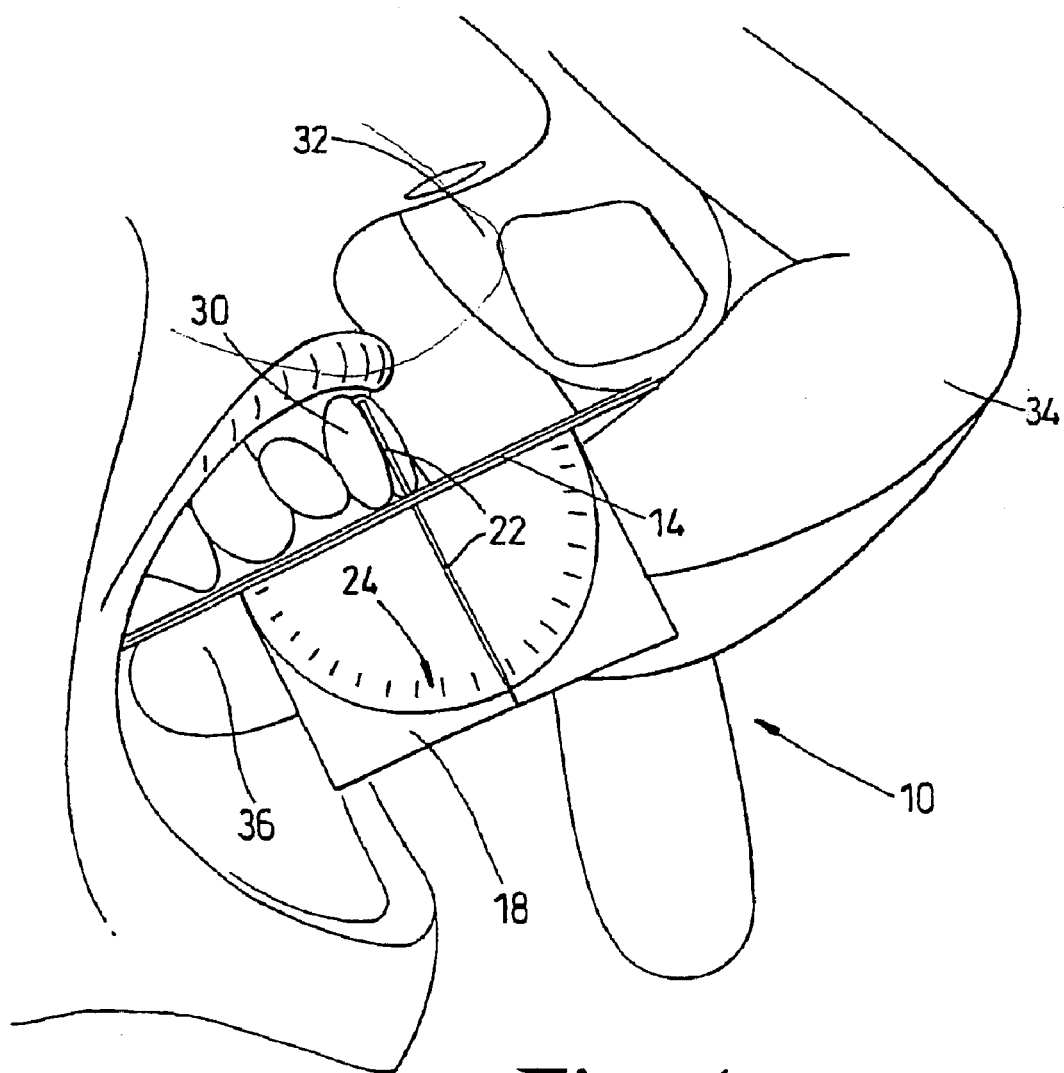
FIG. 4 is a side view similar to FIG. 1, but showing an embodiment of the tooth inclination protractor of this invention in use in a patient's mouth.

The measurement may be taken on a patient directly (FIG. 4) or from a cast taken from the patient's teeth (FIG. 1). In FIG. 4 the device is shown in a patient's mouth held in place by the practitioner's thumb and index and middle fingers 32, 34, 26 respectively.

In addition, the angle of inclination of the tooth may be detected by means other than mechanical, e.g. electronically or by laser or an optical device, such as a solid state sensor which detects the angular disposition of the incisor or the indicator pin.

What is claimed is:

1. A tooth inclination assessment apparatus for allowing assessment of the angle of inclination of an incisor tooth or cast thereof in or from the human or animal body, which apparatus comprise:
    a datum element defining a generally flat datum surface (14) for being placed in use against two or more upper or lower molars or pre-molars thereby to become generally aligned with the respective mandibular or maxillary plane, and
    an angular detector (18-24) associated with said datum element for detecting the angular disposition relative to said datum surface (14) of at least one of the upper or lower incisors respectively,
    characterised in that
    said angular detector (18-24) comprises an indicator member (22) pivotally mounted with respect to said datum surface (14) and extending to opposite sides of said datum surface, to define a tooth contact portion to one side, and a measuring portion to the other, and
    an angle measurement device (18) associated with said datum surface (14) to allow the angle of deflection of the indicator member (22) relative to the datum surface (14) to be determined.

2. A tooth inclination assessment apparatus according to claim 1, wherein said angle measurement device (18) comprises a graduated angular scale (24) whereby the angle of deflection of the indicator member (22) relative to said datum surface (14) may be read off visually.

3. A tooth inclination assessment apparatus according to claim 1, wherein said datum element and said angle measurement device (18) are made up from a folded sheet element blank (12).

4. A tooth inclination assessment apparatus according to claim 3, wherein the blank (12) is made of paper or card.

5. A tooth inclination assessment apparatus according to claim 4, wherein the paper or card is laminated or coated with a waterproof or water resistant coating.

6. A tooth inclination assessment apparatus according to claim 5, wherein the blank (12) is made of plastics material.

7. A tooth inclination assessment apparatus according to claim 3, wherein said sheet element blank (12) comprises two generally symmetric portions which fold together to define said datum element, together with a bridging tab portion (16) which is connected to an angular scale portion defining said angle measurement device.

8. A tooth inclination assessment apparatus to claim 1, wherein said indicator member includes a according shaft (20) which is rotatably located in the fold region between said two symmetric portions.

9. A kit for making a tooth inclination assessment apparatus according to claim 3, comprising said sheet element blank in generally flat form together with an indicator member (22).

10. A tooth inclination assessment apparatus according to claim 1, wherein said datum element and said angle measurement device (18) are integrally formed of moulded plastics material.

11. A method of assessing the angle of inclination of an incisor tooth or a cast thereof in or from the human or animal body, which comprises applying to two or more of the upper molar or lower molars, or pre-molars, a flat datum surface (14) thereby to be generally aligned with the maxillary or mandibular plane respectively, said datum surface (14) having associated therewith an angular detector (18-24) for detecting the angular disposition of at least one of the incisors, and thereby determining the angular orientation of said incisor relative to said datum surface 14, wherein said angular detector (18-24) comprises an indicator member (22) pivotally mounted with respect to said datum surface (14) and extending to opposite sides of said datum surface, to define a tooth contact portion to one side, and a measuring portion to the other, and
    an angle measurement device (18) associated with said datum surface (14) to allow the angle of deflection of the indicator member (22) relative to the datum surface (14) to be determined.

* * * * *